(12) United States Patent
Janssen et al.

(10) Patent No.: US 6,455,748 B2
(45) Date of Patent: Sep. 24, 2002

(54) PROTECTING CATALYTIC ACTIVITY OF A SAPO MOLECULAR SIEVE

(75) Inventors: Marcel J. G. Janssen, Kessel-Lo/Leuven; Cornelius W. M. Van Oorschot, Brasschaat, both of (BE); Shun C. Fung, Bridgewater, NJ (US); Luc R. M. Martens, Meise; Wilfried J. Mortier, Kessel-Lo, both of (BE); Ronald G. Searle, Houston, TX (US); Machteld M. Mertens, Boortmeerbeek (BE); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/760,289

(22) Filed: Jan. 12, 2001

Related U.S. Application Data

(62) Division of application No. 09/391,770, filed on Sep. 8, 1999, now Pat. No. 6,316,683.
(60) Provisional application No. 60/137,933, filed on Jun. 7, 1999.

(51) Int. Cl.$^7$ ................................................ C07C 1/00
(52) U.S. Cl. .................... 585/638; 585/639; 585/640
(58) Field of Search ............................... 585/638, 639, 585/640

(56) References Cited

U.S. PATENT DOCUMENTS

| | | | | |
|---|---|---|---|---|
| 3,893,905 A | * | 7/1975 | Fenske et al. | 208/103 |
| 4,231,899 A | * | 11/1980 | Chen et al. | 502/62 |
| 4,274,982 A | | 6/1981 | Chu | |
| 4,302,565 A | | 11/1981 | Geoke et al. | |
| 4,440,871 A | | 4/1984 | Lok et al. | |
| 4,499,327 A | | 2/1985 | Kaiser | |
| 4,638,106 A | * | 1/1987 | Pieters et al. | 585/640 |
| 4,677,242 A | | 6/1987 | Kaiser | |
| 4,677,243 A | | 6/1987 | Kaiser | |
| 4,681,864 A | * | 7/1987 | Edwards et al. | 502/63 |
| 4,752,651 A | | 6/1988 | Kaiser | |
| 4,842,714 A | | 6/1989 | Pellet et al. | |
| 4,861,938 A | | 8/1989 | Lewis et al. | |
| 5,095,163 A | | 3/1992 | Barger | |
| 5,106,800 A | | 4/1992 | Moser et al. | |
| 5,185,310 A | | 2/1993 | Degnan et al. | |
| 5,191,141 A | | 3/1993 | Barger et al. | |
| 5,248,647 A | * | 9/1993 | Barger | 502/214 |
| 5,264,203 A | | 11/1993 | Beck et al. | |
| 5,554,356 A | * | 9/1996 | Saxton et al. | 423/706 |
| 5,663,471 A | | 9/1997 | Kvisle et al. | |
| 5,714,662 A | | 2/1998 | Vora et al. | |
| 5,714,663 A | | 2/1998 | Serrand et al. | |
| 5,744,680 A | * | 4/1998 | Mulvaney, III et al. | 585/640 |
| 6,005,155 A | * | 12/1999 | Sun | 585/640 |
| 6,023,005 A | * | 2/2000 | Lattner et al. | 585/639 |
| 6,046,371 A | * | 4/2000 | Wu et al. | 585/638 |
| 6,051,745 A | * | 4/2000 | Wu et al. | 585/638 |
| 6,153,798 A | * | 11/2000 | Hidaka et al. | 564/479 |

FOREIGN PATENT DOCUMENTS

| | | |
|---|---|---|
| EP | 0 230 005 A2 | 7/1987 |
| WO | WO 98/29363 | 7/1998 |

OTHER PUBLICATIONS

Methanol Conversion to Light Olefins (Clarence D. Chang) 1984.
Production of Chemicals from Methanol (Warren W. Kaeding & Stephen A. Butter) 1980.
Converting Natural Gas to Ethylene and Propylene by the UOP/Hydro MTO Process (Barger et al.) 12th International Zeolite Conference 1999 Materials Research Society.
The effect of crystallite size on the activity and selectivity of the reaction of ethanol and 2–propanol over SAPO–34, Dahl et al., Microporous and Mesoporous Materials 29 (1999) pp. 159–171.
$^{129}$Xe–NMR Investigation of SAPO–37 (Nathalie Dumont et al.) 1989.
Silicoaluminophosphate Molecular Sieves: Characterization of Textural and Acidic Properties (J. Pires et al.) 1991.
Structural, Acidic and Catalytic Properties of SAPO–11 Molecular Sieves (R. Khouzami et al.).
Influence of the Choice of the Template on the Short–and Long–Term Stability of SAPO–34 Zeolite (M. Briend et al.) 1995.
Synthesis of SAPO–34: High Silicon Incorporation in the Presence of Morpholine as Template (Prakash et al.) 1994.

* cited by examiner

*Primary Examiner*—Walter D. Griffin

(57) ABSTRACT

This invention is directed to a method of making an olefin product from an oxygenate feedstock and a method of protecting catalytic activity of a silicoaluminophosphate molecular sieve. The methods comprise providing a silicoaluminophosphate molecular sieve having catalytic sites within the molecular sieve; shielding the catalytic sites to protect from loss of catalytic activity; and contacting the protected sieve in its activated state with an oxygenate feedstock under conditions effective to produce an olefin product before undesirable loss of catalytic activity. Undesirable loss in catalytic activity occurs when activated molecular sieve contacting the oxygenate feedstock has a methanol uptake index of at least 0.15.

68 Claims, 2 Drawing Sheets

PROTECTING CATALYTIC ACTIVITY OF A SAPO MOLECULAR SIEVE

This application is a divisional of U.S. application Ser. No. 09/391,770 filed Sep. 8, 1999, now U.S. Pat. No. 6,316,683, which claims priority to U.S. Provisional Patent Application No. 60/137,933, filed Jun. 7, 1999, the entire disclosure of which is incorporated herein by reference.

FIELD OF THE INVENTION

This invention relates to a method of protecting the catalytic activity of a SAPO molecular sieve, and to a method of making an olefin product by contacting the activated catalyst with an oxygenate feedstock. In particular, this invention relates to a method of protecting the catalytic activity of a SAPO molecular sieve by shielding the catalytic sites of the molecular sieve.

BACKGROUND OF THE INVENTION

Silicoaluminophosphates (SAPOs) have been used as adsorbents and catalysts. As catalysts, SAPOs have been used in processes such as fluid catalytic cracking, hydrocracking, isomerization, oligomerization, the conversion of alcohols or ethers, and the alkylation of aromatics. In particular, the use of SAPOs in converting alcohols or ethers to olefin products, particularly ethylene and propylene, is becoming of greater interest for large scale, commercial production facilities.

As is known in the development of new large scale, commercial production facilities in the commodity chemical business, many problems arise in the scale up from laboratory and pilot plant operations. This is particularly a concern in catalytic reaction systems where large scale operation will be several orders of magnitude larger than typical pilot scale facilities. For example, conventional laboratory scale processes of making olefin products from oxygenate feed are conducted with catalyst loads of about 5 grams. Conventional large pilot plant operations may utilize as much as 50 kg of catalyst, making on the order of 20 kg/hr ethylene and propylene product, but this is nevertheless minuscule in comparison to what a large scale, commercial production facility would produce, if one were in existence today. It would be desirable to operate large scale, commercial production facilities, which may require a catalyst loading of anywhere from 1,000 kg to 700,000 kg, producing anywhere from 600 to 400,000 kg/hr of ethylene and propylene product, if a reliable method of providing such a large quantity of catalyst could be used.

Operating large scale, commercial production facilities clearly presents great challenges in the development of the catalyst production-to-use chain. By production-to-use chain is meant the entire area of activities beginning with the production of molecular sieve, including such activities as receipt of starting materials, on through the crystallization process. Also included in the production-to-use chain are intermediate activities which include formulation of the sieve with binders and other materials, activation of the manufactured sieve and finished catalyst; storage, transport, loading, unloading of molecular sieve and finished catalyst; as well as other practices associated with the handling and preparation of the sieve and finished catalyst for its ultimate use. The production-to-use chain ends at the point when the molecular sieve is introduced into the reaction system. For purposes of this invention, the end of the production-to-use chain does not necessarily mean the instant when the molecular sieve is introduced into the reaction system, since large scale systems are very large and instantaneous measurements are not practically feasible. In large scale systems, the production-to-use chain may be considered as completed some time within 12 hours of loading an activated catalyst into the reaction system.

Since information to date relating to production of olefin products by catalytic conversion of oxygenate feedstock has been limited to laboratory and small pilot plant activities, little if any attention has been paid to the problems associated with the intermediate activities in the production-to-use chain. For example, little attention has been focused on the impact of storage, transport, etc. on catalyst activity, since small scale activity is rather easily manageable. While today only relatively small quantities of catalyst are stored and transported, large quantities of materials will need to be handled for commercial operations. This may require storage of large quantities of sieve and catalyst materials for considerable periods of time, at multiple locations, and under rather rigorous industrial conditions.

As the management of sieve and catalyst in the catalyst production-to-use chain expands in volume and complexity, there is the likelihood that millions of dollars will be tied up in catalyst inventory, and the value of the sieve and catalyst will be lost if quality is not maintained at every step. Loss of quality will necessarily translate to loss of product quality as well as loss of product quantity, and these product losses could far outweigh the cost of the sieve and catalyst.

Although there has been some work published relating to the intermediate activities in the catalyst production-to-use chain, few of the problems associated therewith have been addressed. For example, U.S. Pat. No. 4,681,864 to Edwards et al. discuss the use of SAPO-37 molecular sieve as a commercial cracking catalyst. It is disclosed that activated SAPO-37 molecular sieve has poor stability, and that stability can be improved by using a particular activation process. In this process, organic template is removed from the core structure of the sieve just prior to contacting with feed to be cracked. The process calls for subjecting the sieve to a temperature of 400–800° C. within the catalytic cracking unit.

U.S. Pat. No. 5,185,310 to Degnan et al. discloses another method of activating silicoaluminophosphate molecular sieve compositions. The method calls for contacting a crystalline silicoaluminophosphate with gel alumina and water, and thereafter heating the mixture to at least 425° C. The heating process is first carried out in the presence of an oxygen depleted gas, and then in the presence of an oxidizing gas. The object of the heating process is to enhance the acid activity of the catalyst. The acid activity is enhanced as a result of the intimate contact between the alumina and the sieve.

Briend et al., *J. Phys. Chem.* 1995, 99, 8270–8276, teach that SAPO-34 loses its crystallinity when the template has been removed from the sieve and the de-templated, activated sieve has been exposed to air. Data are presented, however, which suggest that over at least the short term, this crystallinity loss is reversible. Even over a period of perhaps two years, the data suggest that crystallinity loss is reversible when certain templates are used.

EP-A2-0 203 005 also discusses the use of SAPO-37 molecular sieve in a zeolite catalyst composite as a commercial cracking catalyst. According to the document, if the organic template is retained in the SAPO-37 molecular sieve until a catalyst composite containing zeolite and the SAPO-37 molecular sieve is activated during use, and if thereafter the catalyst is maintained under conditions wherein exposure to moisture is minimized, the crystalline structure of the SAPO-37 zeolite composite remains stable.

As seen from the disclosure herein, we have now found that an activated SAPO molecular sieve will exhibit a loss of catalytic activity when exposed to a moisture-containing environment, and that this loss occurs between the time the catalyst is activated and even after as little as one day of storage. More importantly, we have now found that the loss of catalytic activity is not reversible after a certain period of time. It is desirable, therefore, to obtain an activated SAPO molecular sieve and incorporate that molecular sieve into a catalytic process before loss of catalytic activity becomes too great.

SUMMARY OF THE INVENTION

In order to overcome at least one of the many problems inherent in the prior art, the invention provides a method of protecting catalytic activity of a silicoaluminophosphate molecular sieve which is to be used in converting an oxygenate feedstock to an olefin product, particularly an olefin product comprising ethylene, propylene, or both. Protection against loss of catalytic activity is provided by covering catalytic sites of the molecular sieve with a shield prior to contacting with the oxygenate feedstock. Catalytic contact, i.e., contact of feedstock with molecular sieve under catalytic conversion conditions, must be made before a parameter defined herein as the methanol uptake index drops too low. In addition, the weight percent methanol conversion of the catalyst, determined at standard parameters, should not be allowed to drop below a minimum percentage. Drops in methanol uptake index or methanol conversion which are too low will likely result in a catalyst that is of little or no practical use in a large scale process.

In this invention, the shield can be provided in several ways. The shield can be the template material which is actually used to make the molecular sieve. As is known in the art, the template forms the porous structure within the molecular sieve. Conventionally, the template is removed by calcining, essentially burning it from the molecular sieve. Leaving the template within the intracrystalline structure for the proper time will, however, protect the catalytic sites that are within the porous structure of the molecular sieve.

Even if the template is removed the molecular sieve can still be protected by providing other types of shields to cover the catalytic sites. For example, carbonaceous material can be used as a shield. One way of providing the carbonaceous material is to partially calcine or burn the template, leaving enough carbon material within the pores of the molecular sieve to provide the shield.

An anhydrous environment can also act as a shield, even when the template or carbonaceous material has been removed. An anhydrous environment is one that is depleted in water content. It can be either a gas or a liquid environment.

In a particular embodiment of protecting catalytic activity of a silicoaluminophosphate molecular sieve, the invention comprises providing a silicoaluminophosphate molecular sieve having catalytic sites protected against loss of catalytic activity by covering with a shield, and introducing the molecular sieve into an oxygenate reaction system, wherein the molecular sieve has a methanol uptake index of at least 0.15 at time of contact with oxygenate under conditions effective to convert the oxygenate to olefin product. To provide protection for storage and transportation the shield should be provided within the molecular sieve for at least 12 hours prior to contact with oxygenate. Longer storage and transportation conditions may require that the shield be provided within the molecular sieve for longer periods of time, e.g., 24 hours, 1 month, or perhaps many months.

The protected molecular sieve is of great benefit in large scale commercial processes of making olefin product from oxygenate feedstock, particularly making olefins containing ethylene or propylene from feedstock comprising methanol or dimethyl ether. In a particular embodiment of making an olefin product from an oxygenate feedstock, the invention is to a method which comprises providing a silicoaluminophosphate molecular sieve having catalytic sites within the molecular sieve; providing a shield to protect the catalytic sites from contact with water molecules; removing the shield; and, after removing the shield, contacting the sieve with an oxygenate feedstock under conditions effective to produce an olefin product, wherein the activated sieve contacting the oxygenate feedstock has a methanol uptake index of at least 0.15, preferably 0.4, more preferably at least 0.6, and most preferably at least 0.8.

In another embodiment, there is provided a method of making an olefin product from an oxygenate feedstock, comprising removing a template from a silicoaluminophosphate molecular sieve and contacting the molecular sieve with the oxygenate feedstock under conditions effective to convert the feedstock to an olefin product before the methanol uptake index drops below 0.15, preferably 0.4, more preferably 0.6, most preferably 0.8.

It is desirable that the activated molecular sieve that is contacted with oxygenate feedstock have a methanol conversion of at least 10 wt. % at a standard time on stream (TOS) of 5 minutes and a weight hourly space velocity (WHSV) of 25 $hr^{-1}$. Preferably the molecular sieve should have a methanol conversion of at least 15 wt. % at a standard time on stream of 5 minutes and a WHSV of 25 $hr^{-1}$, more preferably a methanol conversion of at least 20 wt. % at a standard time on stream of 5 minutes and a WHSV of 25 $hr^{-1}$.

The shield can be removed ex situ (outside the reactor per se) or in situ. In a preferred embodiment, the shield is the template and the template is removed outside of the reactor unit per se in order to minimize product contamination, particularly nitrogen contamination due to nitrogen components within a nitrogen-containing template that may be used as the shield.

In another preferred embodiment, once the shield has been removed, the molecular sieve can be maintained at a temperature of at least 150° C., with no shield, with little if any catalyst activity loss due to exposure of catalytic sites with moisture. In this embodiment, the molecular sieve is preferably maintained at a temperature of 150 to 800° C., more preferably at a temperature of 175–600° C., and most preferably at a temperature of 200–500° C. in order to maintain catalyst activity.

Preferably, the template is a nitrogen-containing hydrocarbon. Preferably, the nitrogen-containing hydrocarbon is selected from the group consisting of a tetraethyl ammonium hydroxide salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof. The silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

The oxygenate feedstock is preferably selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. More preferably, the oxygenate feedstock is methanol or dimethyl ether.

The silicoaluminophosphate molecular sieve can provided with a binder material, and the template can be removed by heating at a temperature between 200° C. and 800° C. In order to convert the oxygenate to olefin product, the process is preferably performed at temperature between 200° C. and 700° C.

The present invention will be better understood by reference to the Detailed Description of the Invention when taken together with the attached drawings and the appended claims.

DETAILED DESCRIPTION OF THE INVENTION

Figure 1:
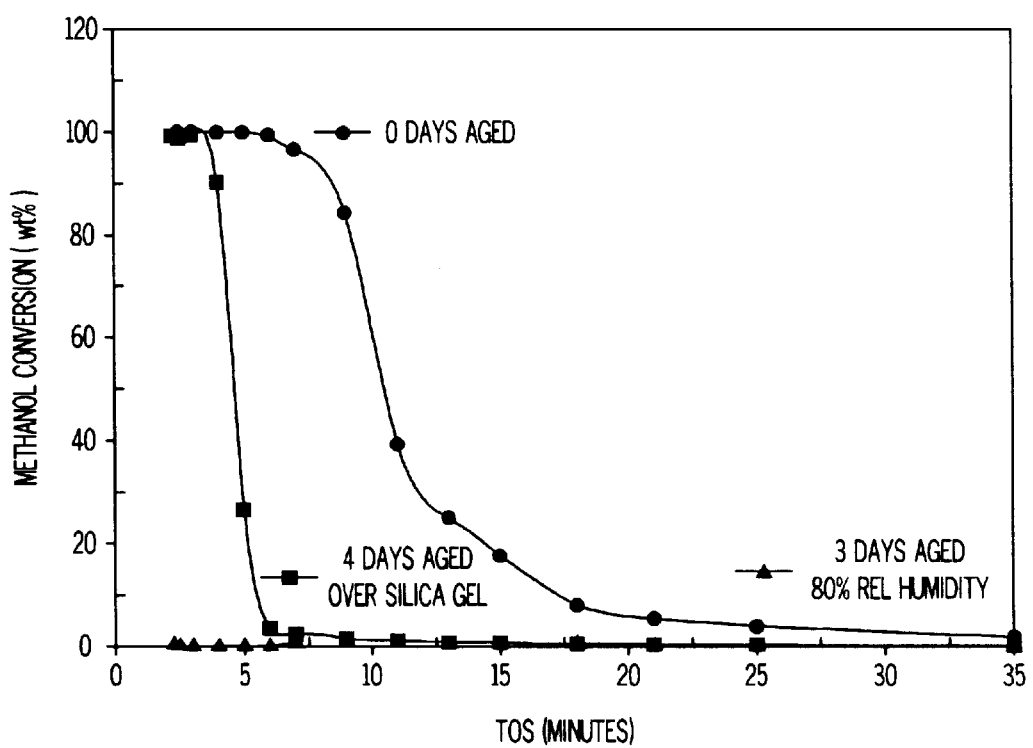
FIG. 1 shows methanol conversion using a morpholine based molecular sieve, which has been aged under various environmental conditions.

SAPO catalysts, in particular, are susceptible to structural changes as a result of continued exposure to even low levels of moisture. Such authorities as Paulitz et al., *Microporous Materials*, 2, 223–228 (1994), however, have shown through X-ray diffraction (XRD), nuclear magnetic resonance (NMR), infrared (IR) and nitrogen (N2) adsorption analyses that the structural change is largely reversible. Nevertheless, we have found that although adsorption analyses indicate that structural change is largely reversible, this data cannot be relied upon as an indicator of loss of catalytic activity. In particular, we have found that SAPO molecular sieves lose catalytic activity when the catalytic sites are exposed to an open air environment for as little as a few hours after activation, and that loss of catalytic activity is irreversible after a certain point.

The possibility of irreversible loss of catalytic activity presents a problem in the commercial production-to-use chain where storage and transport of molecular sieve and catalyst can be over a relatively long period of time. For example, the manufactured molecular sieve can be stored anywhere from 12 hours to many months, perhaps as long as one year, before its final use as an activated catalyst.

SAPO molecular sieve, as well as the SAPO molecular sieve blended with other catalyst material, can be protected from negative effects of moisture by properly shielding catalytic sites within the molecular sieve. Proper shielding can be accomplished in a variety of ways. The catalytic sites can be shielded by maintaining a template within the molecular sieve, by covering the sites with a carbonaceous material or by maintaining the sieve, even without a template, in an anhydrous environment. Removing template or carbonaceous material from the active sites of the molecular sieve results in an activated molecular sieve, meaning that the molecular sieve has its catalytic sites open and ready to contact feedstock. The anhydrous environment serves as a shield for the activated molecular sieve in the sense that it shields active catalyst sites from contact with open air conditions, particularly moisture in the air.

In order to use the SAPO molecular sieve as a catalyst, the shield must be removed such that the catalytic sites of the molecular sieve can be open to contact feedstock. Once the shield is removed, however, the catalytic sites are open to contact with moisture or other components that may be present in the localized environment and cause a loss of catalytic activity. Extended exposure of catalytic sites to such conditions generally results in irreversible loss of catalytic activity to the exposed site. At a certain point, the molecular sieve is not of practical use in a large scale catalytic process. As defined herein, a large scale catalytic process is one having a reactor loading in excess of 50 kg, particularly one having a reactor system loading in excess of 500 kg, especially one having a reactor loading in excess of 5000 kg.

Extended exposure, or the point at which loss of catalytic activity becomes undesirable, is defined according to this invention by a methanol uptake index. According to this invention, the methanol uptake index is defined as the ratio between the maximum methanol adsorption capacity (wt %) of an activated SAPO molecular sieve (i.e., the initial methanol adsorption capacity) and the methanol adsorption capacity (wt %) of the activated SAPO molecular sieve at the time of catalytic contact with a feedstock (i.e., the methanol adsorption capacity at feed contact). At the time of catalytic contact with a feedstock marks the end of the production-to-use chain.

At the time of catalytic contact means the point in time when the activated SAPO molecular sieve is contacted with feed under conditions effective to convert the feed to product, the product containing measurable portions of ethylene and propylene. This does not imply, however, that the methanol adsorption capacity at feed contact must be calculated at the exact instant that feed contacts activated molecular sieve. This is because it may not be possible to run such a precise calculation, particularly in evaluating large scale reaction systems. Therefore, the methanol adsorption capacity at feed contact must be evaluated as soon as practical before contact with feed. For molecular sieve activated in situ, the time between activation and actual contact with feed is short enough such that the initial methanol adsorption capacity is essentially equivalent to the methanol adsorption capacity at feed contact, resulting in a methanol uptake index of approximately 1. For ex situ activation, the methanol adsorption capacity at feed contact should be evaluated as close as practical to actual contact with feed under catalytic conversion conditions. Under some circumstances, especially when dealing with large scale systems, as close as practical may extend up to as much as 12 hours between activation and actual contact with feed under catalytic conversion conditions.

According to this invention, it is preferred that the methanol uptake index be at least 0.15, preferably at least 0.4, more preferably at least 0.6, and most preferably at least 0.8. Although some catalytic activity can occur at a methanol uptake index below 0.15, the molecular sieve at that state is not of practical value as a commercial scale catalyst. Irreversible loss of catalytic activity will likely occur below this point to the extent that the catalyst is no longer of benefit in a large scale catalytic process.

The catalytic activity of the molecular sieve for use as a catalyst for converting oxygenate to olefin product is considered sufficiently preserved or protected when the molecular sieve has the desired methanol uptake index at time of contact with oxygenate under conditions effective to convert the oxygenate to olefin product. Since the methanol uptake index will drop over time if the molecular sieve is improperly handled, contact with oxygenate under reaction conditions should occur before the methanol uptake index drops below 0.15.

To calculate methanol uptake index, methanol adsorption capacity must be measured. Techniques for measuring methanol adsorption capacity are known to those of ordinary skill in the art. In a preferred technique, about 5 mg of sample is introduced into a thermogravimetric analyzer (TGA). The sample is subjected to a heat treatment process, which includes: (1) heating from room temperature to 450° C., with a heat up rate of 20° C./min. in air; (2) holding at 450° C. for 40 min. in air; and cooling to 30° C. in air. After the sample has reached 30° C., the air flow is switched to a methanol containing nitrogen flow with a methanol partial pressure of 0.09 atm. The sample is contacted with this nitrogen/methanol mixture for 180 minutes. The methanol adsorption capacity is the weight percent weight increase after the 180 minutes contact with the methanol vapor.

To obtain a SAPO molecular sieve having the appropriate methanol uptake index, the shield can be removed in situ. That is, the shield, whether template, carbonaceous material or anhydrous liquid or gas, can be removed inside the reactor or the regenerator during operation. However, in a preferred embodiment, the template or carbonaceous material is removed ex situ. This means that it is preferred to activate the catalytic sites of the molecular sieve outside of the reactor. This is because there is less likelihood that the shield material will contaminate the reaction products. This is particularly beneficial when the desired product of the methanol reaction process is to be very low in any nitrogen or sulfur-containing contaminants. For example, in cases where the shield is a molecular sieve template containing a nitrogen component and the desired product of the reaction process is ethylene, it may be desirable to remove the template ex situ since the presence of very small amounts of nitrogen in the ethylene might adversely impact the subsequent conversion of the ethylene product to polyethylene. In less sensitive reaction systems, however, catalyst containing a template material can be added as makeup and activated in situ. Even in more sensitive reaction processes, makeup addition can be directly to the reactor, i.e., in situ addition, since makeup addition can be controlled to add catalyst at relatively low quantities over a period of time, thereby minimizing possible product contamination. Preferably, the makeup addition is directly to a return line which sends regenerated catalyst from the regenerator back to the reactor, or addition is to the regenerator itself Addition of catalyst outside of the reactor itself is considered ex situ addition, which includes addition at the return line or the regenerator.

When ex situ activation of the molecular sieve is carried out, it is important to not let the methanol uptake index drop below the desirable value of 0.15, preferably 0.4, more preferably 0.6, and most preferably 0.8, before using the molecular sieve in a reaction process. As mentioned above, this is because irreversible loss of catalytic activity, which is represented by a significant drop in methanol uptake index as well as methanol conversion, will reach a level that is undesirable for practical operation.

It has also been found that once the activated catalyst is loaded into a heated system, whether reactor, regenerator or any other part of the operating system, or any type of storage environment, loss of catalyst activity is greatly reduced, even when a shield is not present. At a temperature of at least about 150° C., catalyst activity has been found to be stabilized. This means that at a temperature of 150° C. or above, moisture has very little impact on active catalyst sites. It is preferred to maintain active molecular sieve at a temperature of 150 to 800° C., more preferably at a temperature of 175–600° C., and most preferably at a temperature of 200–500° C. in order to maintain catalyst activity.

Undesirable drops in methanol uptake index can be controlled by proper handling during storage or transport. In environments maintained below 150° C., this means that as long as there is sufficient shielding of the catalytic sites before use in a catalytic process, catalytic activity will be acceptable. Sufficient shielding can be maintained by storing or transporting the molecular sieve or catalyst containing the molecular sieve with its template or with an acceptable carbonaceous material which shields the catalytic sites from contact with moisture. Even when activated, sufficient shielding can be maintained by storing or transporting the activated molecular sieve or catalyst containing the molecular sieve in an anhydrous environment.

It is also preferable that the activated SAPO molecular sieve have a methanol conversion of at least 10 wt. %, preferably at least 15 wt. %, most preferably at least 20 wt. %, at standard methanol conversion conditions. For purposes of this invention, standard methanol conversion conditions means that methanol conversion is determined at a time on stream (TOS) of 5 minutes and a WHSV of 24 $hr^{-1}$. As defined herein, methanol conversion is the weight percent of methanol converted to product, with any dimethyl ether present in the product not being included as part of the converted product. The method for calculating methanol conversion is carried out using a standard ½" diameter SS, fixed bed, continuous reactor. A sample of the molecular sieve or a catalyst containing the molecular sieve is added to the reactor and 100% methanol is added as feed. The reaction is carried out at 450° C., a reactor pressure of 25 psig (i.e., a methanol partial pressure of 25 psig), and a weight hourly space velocity (WHSV) of 25 $hr^{-1}$. The reaction products are preferably analyzed with an on-line gas chromatograph (GC). After 5 minutes time on stream (i.e., after 5 minutes of contacting methanol with molecular sieve under reaction conditions), methanol conversion is calculated as: 100−(wt. % methanol+wt. % DME) left in the product.

In testing for the methanol conversion, WHSV is defined as the weight of the feed fed to the ½" reactor over time (per hour) divided by the weight of the silicoaluminophosphate molecular sieve component of the catalyst in the reactor. The silicoaluminophosphate molecular sieve component of the catalyst is intended to mean only the silicoaluminophosphate molecular sieve portion that is contained within the catalyst. This excludes catalyst components such as non-silicoaluminophosphate molecular sieves, binders, diluents, inerts, rare earth components, etc.

The silicoaluminophosphate molecular sieves of this invention comprise a three-dimensional microporous crystal framework structure of $[SiO_2]$, $[AlO_2]$ and $[PO_2]$ tetrahedral units. The way Si is incorporated into the structure can be determined by $^{29}$Si MAS NMR. See Blackwell and Patton, *J. Phys. Chem.*, 92, 3965 (1988). The desired SAPO molecular sieves will exhibit one or more peaks in the $^{29}$Si MAS NMR, with a chemical shift [(Si)] in the range of −88 to −94 ppm and with a combined peak area in that range of at least 20% of the total peak area of all peaks with a chemical shift [(Si)] in the range of −88 ppm to −115 ppm, where the [(Si)] chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid. organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +3. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, however, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system.

The SAPO molecular sieve can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

In this invention, the templates can be used to shield the catalytic sites of the SAPO molecular sieve from contact with water molecules. Since the templates will be present within the microporous structure of the sieve, water molecules will not be able to enter the pores of the sieve, preventing any contact with the catalyst sites. This means that a molecular sieve containing a template can even be stored in wet filter cake form, without noticeable loss of catalytic activity once activated. When stored in wet filter cake form, the molecular sieve will typically be dried without removing the template. Then, the molecular sieve can be calcined to remove the template.

Carbonaceous material can also be used to shield the catalytic sites of the SAPO molecular sieve. In this embodiment, carbonaceous material can be within the microcrystalline pore structure or it can be deposited to cover the pore entrance. The carbonaceous material can be placed within the crystalline pore structure by partially burning the template material so that carbon residue remains within the molecular sieve. Carbonaceous material can also be directly applied to the exterior of the molecular sieve to block the pore openings.

As is known in the art, molecular sieve or catalyst containing the molecular sieve, must be activated prior to use in a catalytic process. Activation is performed in such a manner that template is removed from the molecular sieve, leaving active catalytic sites with the microporous channels of the molecular sieve open for contact with feed. The activation process is typically accomplished by calcining, or essentially heating the template at a temperature of from 200 to 800° C. in the presence of an oxygen-containing gas. In some cases, it may be desirable to heat in an environment having a low oxygen concentration. This type of process can be used for partial or complete removal of the template from the intracrystalline pore system. In other cases, particularly with smaller templates, complete or partial removal from the sieve can be accomplished by conventional desorption processes such as those used in making standard zeolites.

Once the molecular sieve or catalyst containing the molecular sieve has been activated, an anhydrous environment can be provided as a shield against water molecules contacting catalyst sites within the molecular sieve. Such an environment can be provided by covering the sieve with a gas or liquid blanket under anhydrous conditions. As provided herein, the anhydrous gas or liquid blanket will have a limited amount of water. The anhydrous gas blanket can be provided under vacuum conditions or under atmospheric or greater pressure conditions, and will have less than about 1.2 volume percent water, preferably less than about 0.2 volume percent water, more preferably less than about 0.02 volume percent water. The anhydrous liquid blanket will have less than about 200 ppm water preferably less than about 100 ppm water, more preferably less than about 50 ppm water. The anhydrous environment can be applied during storage, transport or loading of the catalyst.

The anhydrous gas blanket is one which is a gas under standard temperature and pressure conditions and does not react to any significant degree with the molecular sieve structure. The gas is preferably selected from the group consisting of nitrogen, helium, CO, $CO_2$, $H_2$, argon, $O_2$, light alkanes (especially $C_1$–$C_4$ alkanes, particularly methane and ethane), cyclo-alkanes and mixtures thereof, e.g. air. The gas blanket can be maintained at any pressure, including under vacuum or at pressures above standard, even if the gas becomes liquid at pressures above standard, as long as the conditions remain anhydrous.

The anhydrous liquid blanket is a liquid under standard temperature and pressure conditions, and does not react to any significant degree with the molecular sieve structure. The liquid is preferably selected from the group consisting of alkanes, cyclo-alkanes, $C_6$–$C_{30}$ aromatics, alcohols, particularly $C_4^+$ branched alcohols.

In this invention, the molecular sieve is made ready for use in a catalytic process by removing the shielding conditions. If the gas or liquid blanket is applied under anhydrous conditions to shield an already activated molecular sieve, the blanket or liquid need merely be removed by any standard technique. This can be as simple as merely opening the blanketed system to the atmosphere or by using any standard filtration or separation technique.

If a carbonaceous material is used as the shield, it can also be removed by exposing the sieve to sufficient temperature conditions to decompose the carbonaceous material. Preferably, the carbonaceous material is removed by calcining at a temperature of about 200–800° C.

It is preferred that the molecular sieve not be exposed to hydrous conditions once the shield is removed. Otherwise, there may be irreversible catalytic loss. However, the molecular sieve can be stored, transported or loaded into a reactor system, in its unshielded form, in a hydrous environment as long as the methanol uptake index does not fall below 0.15, preferably 0.4, more preferably 0.6, most preferably 0.8.

The silicoaluminophosphate molecular sieves may be admixed (blended) with other materials. When blended, the resulting composition is typically referred to as a silicoaluminophosphate (SAPO) catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve which is contained in the final catalyst product ranges from 10 to 90 weight percent of the total catalyst, preferably 30 to 70 weight percent of the total catalyst.

In one embodiment of this invention, a feed containing an oxygenate is contacted in a reaction zone of a reactor apparatus with an activated molecular sieve catalyst at process conditions effective to produce light olefins, i.e., an effective temperature, pressure, WHSV (weight hour space velocity) and, optionally, an effective amount of diluent, correlated to produce light olefins. Typically, the oxygenate feed is contacted with the catalyst when the oxygenate is in a vapor phase. However, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 500° C. is preferred.

Owing to the nature of the process, it may be desirable to carry out the process of the present invention by use of the molecular sieve catalysts in a dynamic bed system or any system of a variety of transport beds rather than in a fixed bed system. It is particularly desirable to operate the reaction process at high space velocities.

The conversion of oxygenates to produce light olefins may be carried out in a variety of large scale catalytic reactors, including, but not limited to, fluid bed reactors and concurrent riser reactors as described in "Free Fall Reactor,"

*Fluidization Engineering,* D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems,* pages 48–59, F. A. Zenz and D. F. Othmo, Reinhold Publishing Corp., NY 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 $hr^{-1}$ to 1000 $hr^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

It is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, pressures of from about 0.1 kPa to about 10 MPa. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

One or more inert diluents may be present in the feedstock, for example, in an amount of from 1 to 99 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst. When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols, their unsaturated counterparts and the nitrogen, halogen and sulfur analogues of such. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

This invention will be better understood with reference to the following examples, which are intended to illustrate specific embodiments within the overall scope of the invention as claimed.

EXAMPLE 1

Samples of SAPO-34 containing a morpholine template were heated in order to remove the template. One sample was heated for 5 hours at 650° C. in $N_2$ followed by 3 hours at 650° C. in air in a closed furnace to remove the template. The sample was stored for 4 days over silica gel (relative humidity <20% at 20° C.). A second sample was heated in the same manner, but was stored for 3 days at 80% relative humidity and 20° C. In a third sample, the template was removed in the same manner. However, the third sample was transferred at 150° C. into a fixed bed, continuous reactor immediately after template removal. The third sample was designated as the "0 days aged" sample portion. Each portion was then individually evaluated in a fixed bed, continuous reactor. Reaction temperature was maintained at 450° C. Pressure in the reactor was held at 25 psig. Methanol feed was continuously fed to the reactor at a WHSV of 25 $hr^{-1}$. Reaction products were analyzed with an on-line GC equipped with a FID and TCD detector. FIG. 1 shows wt % of methanol converted as a function of TOS (in minutes). The methanol conversion of the first sample at a TOS of 5 minutes was approximately 27 wt. %. The methanol conversion of the second sample at a TOS of 5 minutes was approximately 0 wt. %. the methanol conversion of the third sample at TOS of 5 minutes was approximately 100 wt. %.

EXAMPLE 2

Samples of SAPO-34 containing a morpholine template were heated in order to remove the template. One sample was heated for 5 hours at 650° C. in $N_2$ followed by 3 hours at 650° C. in air in a closed furnace to remove the template. The sample was stored for 1 day under ambient conditions. A second sample was heated in the same manner, but was stored for 5 days under ambient conditions. In a third sample, the template was removed in situ (i.e., in a fixed bed, continuous reactor) under nitrogen at 650° C. for 5 hours, followed by air at 650° C. for 3 hours. The third sample was designated as the "0 days aged" sample portion. The sample portions having the templates removed were measured for methanol uptake according to the following procedure.

Figure 2:
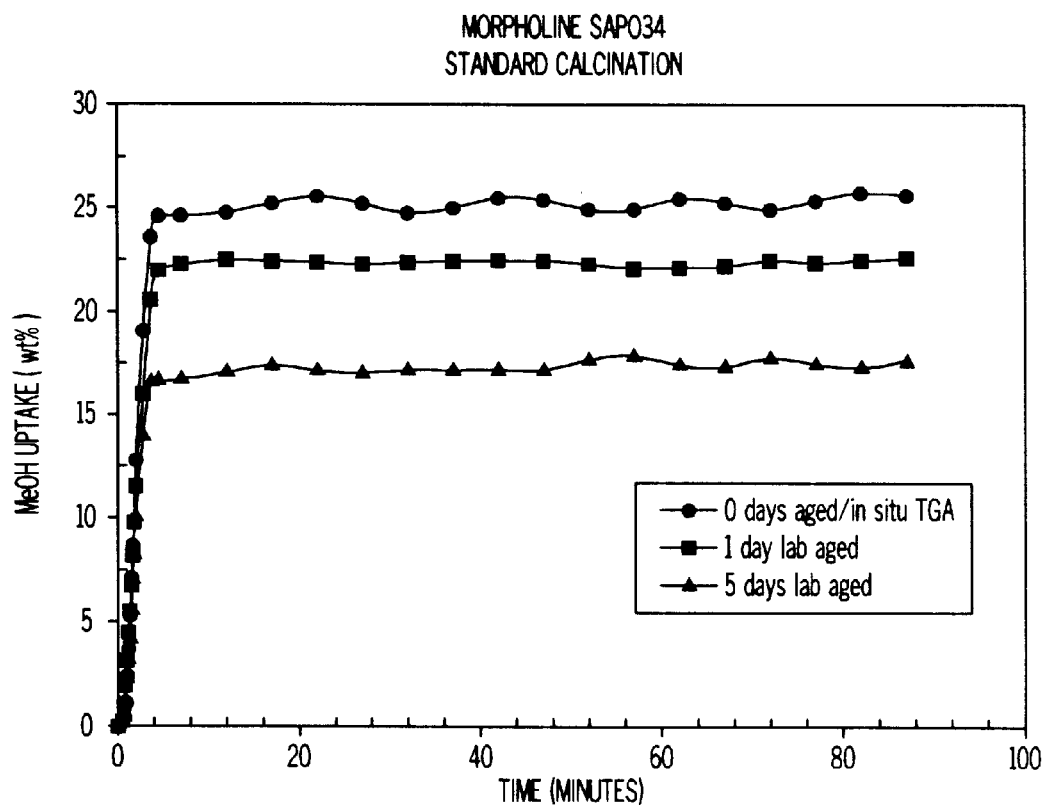
FIG. 2 shows methanol uptake of a morpholine based molecular sieve.

About 5 mg of sample was introduced into a Perkin Elmer TGS-2 thermogravimetric analyzer (TGA). The sample was subjected to heat treatment, which included: (1) heating from room temperature to 450° C., with a heat up rate of 20° C./min. in air; (2) holding at 450° C. for 40 min. in air; and cooling to 30° C. in air. After the sample reached 30° C., the air flow was switched to a methanol containing nitrogen flow with a methanol partial pressure of 0.09 atm. The sample was then contacted with this nitrogen/methanol mixture for 180 minutes, and the methanol adsorption capacity was calculated as the weight percent increase after the 180 minutes contact with the methanol vapor. FIG. 2 shows methanol adsorption capacity or methanol uptake as a function of time. The horizontal line fragments indicate the saturation level.

The methanol uptake index was calculated based on the saturation level aged samples versus the saturation level of the "0 days aged/in situ" sample. The 0 days aged/in situ sample was defined as the base case, having a methanol uptake index of 1. The methanol uptake index for the 1 day lab aged sample was calculated as approximately 0.85, and the methanol uptake index for the 5 days lab aged sample was calculated as approximately 0.65.

EXAMPLE 3

Figure 3:
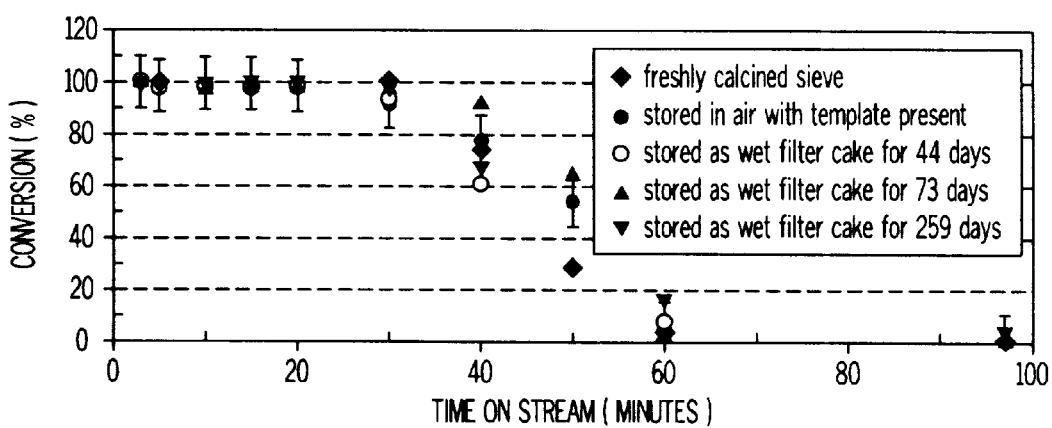
FIG. 3 shows methanol conversion using a SAPO-34 molecular sieve which has been stored under various conditions.

A sample of SAPO-34 containing a DPA/TEAOH template was dried, with the template being left in place. The sample was stored for 25 days, then mixed with SiC (0.36 g SAPO/5 g SiC). The template was then removed in situ (i.e., in a fixed bed, continuous reactor) under nitrogen at 625° C. for 1 hour. After template removal, methanol was continuously fed to the reactor at a WHSV of 25 $hr^{-1}$ while maintaining the reaction temperature at 450° C. and the reactor pressure at 23 psig. Reaction products were analyzed with an on-line GC equipped with a FID and TCD detector for ethylene and propylene yield. Methanol conversion was calculated as: 100−(wt % methanol+DME) left in product. The data are shown in FIG. 3, with the label "fresh, calcined sieve."

EXAMPLE 4

A sample of SAPO-34 containing a DPA/TEAOH template was filtered and stored in a wet filter cake form, with the template being left in place. After storing for 44 days, the filter cake was dried, then the template was then removed and methanol conversion calculated according to the procedure of Example 3. The data are shown in FIG. 3.

EXAMPLE 5

A sample of SAPO-34 containing a DPA/TEAOH template was filtered and stored in a wet filter cake form, with the template being left in place. After storing for 73 days, the filter cake was dried, then the template was then removed and methanol conversion calculated according to the procedure of Example 3. The data are shown in FIG. 3.

EXAMPLE 6

A sample of SAPO-34 containing a DPA/TEAOH template was dried, with the template being left in place. The sample was stored for 132 days under ambient conditions. The template was then removed and methanol conversion calculated according to the procedure of Example 3. The data are shown in FIG. 3.

EXAMPLE 7

A detemplated SAPO-34 was aged under ambient conditions for 18 months. Methanol adsorption capacity was determined according to the procedure of Example 2. From the initial methanol adsorption capacity and the methanol adsorption capacity at feed contact, the methanol uptake index was calculated as 0.12.

Methanol conversion of a sample of the 18 months aged SAPO-34 was evaluated according to the procedure of Example 3. At a TOS of 2 minutes, the methanol conversion was 26.97 wt. %. At a TOS of 5 minutes, the methanol conversion had significantly dropped to 0.63 wt. %.

The data indicate that a silicoaluminophosphate molecular sieve having a methanol uptake index of 0.12 is catalytically active for a brief period of time. However, the catalytic activity of such a molecular sieve drops off very quickly, indicating that a molecular sieve having such a low methanol uptake index is less desirable for reaction systems, as it will tend to increase the frequency at which the molecular sieve will need to be regenerated.

Having now fully described this invention, it will be appreciated by those skilled in the art that the invention can be performed within a wide range of parameters within what is claimed, without departing from the spirit and scope of the invention.

What is claimed is:

1. A method of making an olefin product from an oxygenate feedstock, comprising providing a silicoaluminophosphate molecular sieve having catalytic sites within the molecular sieve; providing a shield to protect the catalytic sites from contact with water molecules, wherein the shield is a carbonaceous material; removing the shield; and, after removing the shield, contacting the sieve with an oxygenate feedstock under conditions effective to produce an olefin product, wherein the sieve contacting the oxygenate feedstock has a methanol uptake index of at least 0.15.

2. The method of claim 1, wherein the methanol uptake index is at least 0.4.

3. The method of claim 2, wherein the methanol uptake index is at least 0.6.

4. The method of claim 3, wherein the methanol uptake index is at least 0.8.

5. The method of claim 1, wherein the sieve contacting the feedstock has a methanol conversion of at least 10 wt. % at a standard time on stream of 5 minutes and a WHSV of 25 $hr^{-1}$.

6. The method of claim 5, wherein the sieve contacting the feedstock has a methanol conversion of at least 15 wt. % at a standard time on stream of 5 minutes and a WHSV of 25 $hr^{-1}$.

7. The method of claim 6, wherein the sieve contacting the feedstock has a methanol conversion of at least 20 wt. % at a standard time on stream of 5 minutes and a WHSV of 25 $hr^{-1}$.

8. The method of claim 1, wherein the sieve is maintained at a temperature of at least 150° C. prior to contacting with feedstock.

9. The method of claim 1, wherein the shield is removed ex situ.

10. The method of claim 1, wherein the shield is removed in situ.

11. The method of claim 1, wherein the shield is a carbon residue of a template.

12. The method of claim 11, wherein the template is selected from the group consisting of a tetraethyl ammonium salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

13. The method of claim 11, further comprising partially burning the template to form the carbon residue.

14. The method of claim 11, wherein the template is provided with the molecular sieve as a wet filter cake.

15. The method of claim 1, further comprising directly applying the carbonaceous material to the exterior of the molecular sieve.

16. The method of claim 1, wherein the molecular sieve has a pore size of less than 5 angstroms.

17. The method of claim 1, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and metal containing forms thereof.

18. The method of claim 1, wherein the activated catalyst is contacted with the oxygenate feedstock in a reactor at a WHSV of 1 $hr^{-1}$ to 1000 $hr^{-1}$.

19. The method of claim 18, wherein olefins are produced at a TCNMS of less than 0.016.

20. The method of claim 1, wherein the molecular sieve is contacted with the oxygenate feedstock at a pressure of from 0.1 kPa to 100 MPa 21. The method of claim 1, wherein the oxygenate feedstock is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

22. The method of claim 1, wherein the olefin product comprises ethylene, propylene, or a combination thereof.

23. The method of claim 1, wherein the silicoaluminophosphate molecular sieve is provided with a binder material.

24. The method of claim 1, wherein the olefin product is contacted with a polyolefin-forming catalyst under conditions effective to form a polyolefin.

25. A method of storing a silicoaluminophosphate molecular sieve and making an olefin from an oxygenate feedstock using the stored molecular sieve, comprising storing a silicoaluminophosphate molecular sieve in the form of a wet filter cake, the stored molecular sieve having a template therein; drying the stored molecular sieve; calcining the dried molecular sieve to remove the template and form an activated molecular sieve; and contacting the activated molecular sieve with an oxygenate feedstock under conditions effective to produce an olefin product, the activated molecular sieve contacting the oxygenate feedstock having a methanol uptake index of at least 0.15.

26. The method of claim 25, wherein the template is selected from the group consisting of tetraethyl ammonium salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

27. The method of claim 25, wherein the silicoaluminophosphate molecular sieve has a pore size of less than 5 angstroms.

28. The method of claim 25, wherein the silicoaluminophosphate molecular sieve is selected from the group consisting of SAPO-18, SAPO-34, SAPO-35, SAPO-44, SAPO-47 and SAPO-56, including the metal containing forms thereof, and mixtures thereof.

29. The method of claim 25, wherein the dried molecular sieve is calcined by heating a temperature between 200° C. and 800° C.

30. The method of claim 29, wherein the dried molecular sieve is calcined by heating a temperature between 200° C. and 700° C.

31. The method of claim 25, wherein the dried molecular sieve is calcined by contacting with an oxygen-containing gas.

32. The method of claim 25, wherein the olefin product is made inside a reactor.

33. The method of claim 32, wherein the calcination is inside the reactor.

34. The method of claim 32, wherein the calcination is outside the reactor.

35. The method of claim 32, wherein the activated molecular sieve is contacted with oxygenate feedstock in a reactor at a WHSV of 1 $hr^{-1}$ to 1000 $hr^{-1}$.

36. The method of claim 25, wherein the calcination is inside a regenerator.

37. The method of claim 25, wherein the activated molecular sieve is maintained at a temperature of at least 150° C. prior to contacting with the oxygenate feedstock.

38. The method of claim 25, wherein 50 kg of molecular sieve is stored.

39. The method of claim 25, wherein 500 kg of molecular sieve is stored.

40. The method of claim 25, wherein 5000 kg of molecular sieve is stored.

41. The method of claim 25, wherein the oxygenate is selected from the group consisting of methanol, dimethyl ether and mixtures thereof.

42. The method of claim 25, wherein the olefins are produced at a TCNMS of less than 0.016.

43. The method of claim 25, wherein the activated molecular sieve is contacted with the oxygenate feedstock at a pressure of from 0.1 kPa to 10 MPa.

44. The method of claim 25, wherein the olefin product comprises a compound selected from the group consisting of ethylene, propylene, or a combination thereof.

45. The method of claim 25, wherein the dried molecular sieve is partially calcined, leaving enough carbon material within the molecular sieve to shield catalytic sites within the molecular sieve.

46. The method of claim 45, wherein the dried molecular sieve is calcined at a temperature between 200° C. and 800° C., resulting in an activated molecular sieve ready to contact the oxygenate feedstock.

47. The method of claim 25, further comprising, after calcination of the dried molecular sieve, creating a shielding condition by providing an anhydrous environment as a shield against water molecules contacting catalyst sites within the activated molecular sieve, and removing the shielding condition to make the activated molecular sieve ready for catalytic use.

48. The method of claim 47, wherein the anhydrous environment is provided by covering the sieve with a gas blanket under anhydrous conditions.

49. The method of claim 48, wherein the anhydrous gas blanket is provided under vacuum conditions.

50. The method of claim 48, wherein the anhydrous gas blanket is provided under atmospheric pressure conditions.

51. The method of claim 48, wherein the anhydrous gas blanket is provided under greater than atmospheric pressure conditions.

52. The method of claim 48, wherein the anhydrous gas blanket is provided under conditions having less than 1.2 volume percent water.

53. The method of claim 50, wherein the anhydrous gas blanket is provided under conditions having less than 0.2 volume percent water.

54. The method of claim 53, wherein the anhydrous gas blanket is provided under conditions having less than 0.02 volume percent water.

55. The method of claim 47, wherein the anhydrous environment is provided by covering the sieve with a liquid blanket under anhydrous conditions.

56. The method of claim 55, wherein the anhydrous liquid blanket is provided under vacuum conditions.

57. The method of claim 55, wherein the anhydrous liquid blanket is provided under atmospheric pressure conditions.

58. The method of claim 55, wherein the anhydrous liquid blanket is provided under greater than atmospheric pressure conditions.

59. The method of claim 55, wherein the anhydrous liquid blanket is provided under conditions having less than 1.2 volume percent water.

60. The method of claim 55, wherein the anhydrous liquid blanket is provided under conditions having less than 0.2 volume percent water.

61. The method of claim 55, wherein the anhydrous liquid blanket is provided under conditions having less than 0.02 volume percent water.

62. The method of claim 48, wherein the anhydrous gas blanket comprises a gas selected from the group consisting of air, nitrogen, helium, CO, $CO_2$, $H_2$, argon, $O_2$, $C_1$–$C_4$ alkanes, cycloalkanes and mixtures thereof.

63. The method of claim 62, wherein the gas is nitrogen.

64. The method of claim 55, wherein the anhydrous liquid blanket has less than about 200 ppm water.

65. The method of claim 64, wherein the anhydrous liquid blanket has less than about 100 ppm water.

66. The method of claim 65, wherein the anhydrous liquid blanket has less than about 50 ppm water.

67. The method of claim 55, wherein the anhydrous liquid blanket comprises a liquid selected from the group consisting of alkanes, cycloalkanes, $C_6$–$C_{30}$ aromatics and alcohols.

68. The method of claim 25, wherein the silicoaluminophosphate molecular sieve is mixed with other materials, as a catalyst comprising the silicoaluminophosphate molecular sieve.

* * * * *